United States Patent [19]

Liu

[11] 4,435,588

[45] Mar. 6, 1984

[54] HERBICIDAL COMPOUNDS, COMPOSITIONS, AND METHOD OF USE

[75] Inventor: Kou-chang Liu, Wayne, N.J.

[73] Assignee: GAF Corporation, New York, N.Y.

[21] Appl. No.: 283,402

[22] Filed: Jul. 15, 1981

[51] Int. Cl.³ .............................................. C07C 69/76
[52] U.S. Cl. ....................... 500/21; 71/107; 71/94; 260/455 R; 260/465 D; 260/507 R; 564/166
[58] Field of Search ............................. 560/21; 71/107

[56] References Cited

U.S. PATENT DOCUMENTS 3,282,991  11/1966  Klein et al. ........................... 560/51

FOREIGN PATENT DOCUMENTS 2950401  2/1981  Fed. Rep. of Germany ........ 560/21

*Primary Examiner*—Paul J. Killos
*Attorney, Agent, or Firm*—Marilyn J. Maue; J. Gary Mohr; Joshua J. Ward

[57] ABSTRACT

Novel and highly effective herbicidal compounds in the diphenylether class are provided herein.

32 Claims, No Drawings

HERBICIDAL COMPOUNDS, COMPOSITIONS, AND METHOD OF USE

BACKGROUND OF THE INVENTION

1. Field of the Invention

This invention relates to novel compounds which are active herbicides.

2. Description of the Prior Art

Certain phenoxybenzoates show herbicidal activity and are disclosed in e.g. U.S. Pat. Nos. 3,652,645; 3,784,635; 3,798,276; 3,928,416; 3,941,830; 3,979,437; 4,001,005; 4,002,662; 4,046,798; 4,063,929; 4,164,408; 4,164,409; 4,164,410; 4,178,169 and 4,185,995. However, the herbicidal effectiveness and selectivity of a given phenoxybenzoate cannot be predicted from an examination of its chemical structure. Often quite closely related compounds will have quite different weed control abilities and crop selectivity.

SUMMARY OF THE INVENTION

In accordance with the present invention, there is provided novel herbicidal phenoxybenzoates having the formula:

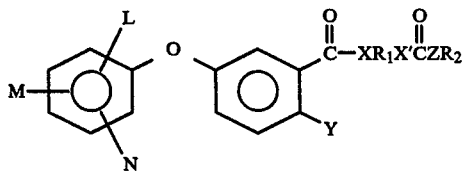

where:

L, M and N are independently hydrogen, halogen, trihalomethyl, nitro, cyano,

hydroxy, alkoxy $C_1$–$C_4$, or alkyl $C_1$–$C_4$;

X and X' are independently oxygen, sulfur or —$NR_5$;

$R_1$ is a saturated or unsaturated, straight or branched chain aliphatic diradical $C_1$–$C_{18}$ wherein one or more of the methylene group may be replaced by oxygen, sulfur, disulfur, —SO—, —$SO_2$—, or —$NR_6$; where the aliphatic diradical may be optionally substituted with halogen, trihalomethyl, cyano, hydroxy, alkoxy, aryl, cyano or a cyclic alkyl $C_3$–$C_6$;

Z is oxygen, sulfur, $NR_7$, or a direct bond;

$R_2$ is a saturated or unsaturated, straight or branched chain aliphatic radical $C_1$–$C_8$ optionally substituted with halogen, trihalomethyl, cyano, nitro, hydroxy, acetoxy, alkoxy, thioalkoxy or aryl; an aryl radical optionally substituted with halogen, trihalomethyl, cyano, nitro, alkyl, alkoxy or hydroxy;

a cyclic alkylene or alkenylene ring $C_3$–$C_6$ optionally substituted with halogen, trihalomethyl, hydroxy, alkyl, alkoxy or cyano;

Y is nitro, cyano, halogen or

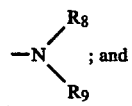; and $R_3$, $R_4$, $R_5$, $R_6$, $R_7$, $R_8$ and $R_9$ are independently hydrogen, a saturated or unsaturated, straight or branched chain aliphatic radical $C_1$–$C_8$ optionally substituted with halogen, hydroxy, alkoxy, cyano or nitro.

The novel compounds of the invention have been found to show excellent activity as weed control agents towards major agricultural crops.

Non-limiting examples of the compounds of this invention embraced within the formula are given in Table I below:

TABLE I

| Ex. No. | Compound | L | M | N | X | X' | Y | R | ZR₂ |
|---|---|---|---|---|---|---|---|---|---|
| 1 | 2-(Chloroacetoxy)ethyl 5-(2-chloro-4-trifluoromethylphenoxy)-2-nitrobenzoate | 2-Cl | 4-CF₃ | H | O | O | NO₂ | —CH₂CH₂— | —CH₂Cl |
| 2 | 2-Acetoxyethyl 5-(2-chloro-4-trifluoromethylphenoxy)-2-nitrobenzoate | 2-Cl | 4-CF₃ | H | O | O | NO₂ | —CH₂CH₂— | —CH₃ |
| 3 | 2-(Isobutyryloxy)ethyl 5-(2-chloro-4-trifluoromethylphenoxy)-2-nitrobenzoate | 2-Cl | 4-CF₃ | H | O | O | NO₂ | —CH₂CH₂— | 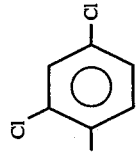 |
| 4 | 2-(Cyclopropanecarboxy)ethyl 5-(2-chloro-4-trifluoromethylphenoxy)-2-nitrobenzoate | 2-Cl | 4-CF₃ | H | O | O | NO₂ | —CH₂CH₂— |  |
| 5 | 2-(Acryloyloxy)ethyl 5-(2-chloro-4-trifluoromethylphenoxy)-2-nitrobenzoate | 2-Cl | 4-CF₃ | H | O | O | NO₂ | —CH₂CH₂— | —CH=CH₂ |
| 6 | 2-(Methoxyacetoxy)ethyl 5-(2-chloro-4-trifluoromethylphenoxy)-2-nitrobenzoate | 2-Cl | 4-CF₃ | H | O | O | NO₂ | —CH₂CH₂— | —CH₂OCH₃— |
| 7 | 3-Acetoxypropyl 5-(2-chloro-4-trifluoromethylphenoxy)-2-nitrobenzoate | 2-Cl | 4-CF₃ | H | O | O | NO₂ | —CH₂CH₂CH₂— | —CH₃ |
| 8 | 4-(Chloroacetoxy)butyl 5-(2-chloro-4-trifluoromethylphenoxy)-2-nitrobenzoate | 2-Cl | 4-CF₃ | H | O | O | NO₂ | —CH₂CH₂CH₂CH₂— | —CH₂Cl |
| 9 | 2-(3-Chlorobenzoyloxy)ethyl 5-(2-chloro-4-trifluoromethylphenoxy)-2-nitrobenzoate | 2-Cl | 4-CF₃ | H | O | O | NO₂ | —CH₂CH₂— | 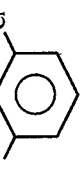 |
| 10 | 2-(2,4-Dichlorobenzoyloxy)ethyl 5-(2-chloro-4-trifluoromethylphenoxy)-2-nitrobenzoate | 2-Cl | 4-CF₃ | H | O | O | NO₂ | —CH₂CH₂— | 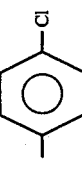 |
| 11 | 4-Acetoxy-2-buten-1-yl 5-(2-chloro-4-trifluoromethylphenoxy)-2-nitrobenzoate | 2-Cl | 4-CF₃ | H | O | O | NO₂ | —CH₂CH=CHCH₂— | —CH₃ |
| 12 | 11-Chloroacetoxy-3,6,9-trioxaundecyl 5-(2-chloro- | 2-Cl | 4-CF₃ | H | O | O | NO₂ | —(CH₂CH₂O)₃CH₂CH₂— | —CH₂Cl |

TABLE I-continued

| Ex. No. | Compound | L | M | N | X | X' | Y | R | ZR₂ |
|---|---|---|---|---|---|---|---|---|---|
| | 4-trifluoromethylphenoxy)-2-nitrobenzoate | | | | | | | | |
| 13 | 2-Benzoyloxyethyl 5-(2-chloro-4-trifluoromethyl-phenoxy)-2-nitrobenzoate | 2-Cl | 4-CF₃ | H | O | O | NO₂ | —CH₂CH₂— | phenyl |
| 14 | 6-Acetoxy-3,4-dithiahexyl 5-(2-chloro-4-trifluoromethylphenoxy)-2-nitrobenzoate | 2-Cl | 4-CF₃ | H | O | O | NO₂ | —CH₂CH₂—S—S—CH₂CH₂— | —CH₃ |
| 15 | 2-(3-Amino-2,5-dichlorobenzoyloxy)ethyl 5-(2-chloro-4-trifluoromethylphenoxy)-2-nitrobenzoate | 2-Cl | 4-CF₃ | H | O | O | NO₂ | —CH₂CH₂— | 3-amino-2,5-dichloro-4-methylphenyl |
| 16 | 2-(Propionyloxy)ethyl 5-(2-chloro-4-trifluoromethyl-phenoxy)-2-nitrobenzoate | 2-Cl | 4-CF₃ | H | O | O | NO₂ | —CH₂CH₂— | —CH₂CH₃ |
| 17 | 2-(Trifluoroacetoxy)ethyl 5-(2-chloro-4-trifluoromethylphenoxy)-2-nitrobenzoate | 2-Cl | 4-CF₃ | H | O | O | NO₂ | —CH₂CH₂— | —CF₃ |
| 18 | 5-(Chloroacetoxy)-3-oxapentyl 5-(2-chloro-4-trifluoromethylphenoxy)-2-nitrobenzoate | 2-Cl | 4-CF₃ | H | O | O | NO₂ | —CH₂CH₂OCH₂CH₂— | —CH₂Cl |
| 19 | 6-(N,N—Dimethylcarbamyloxy)hexyl 5-(2-chloro-4-trifluoromethylphenoxy)-2-nitrobenzoate | 2-Cl | 4-CF₃ | H | O | O | NO₂ | —(CH₂)₆— | —N(CH₃)₂ |
| 20 | 2-(N,N—Dimethylcarbamyloxy)ethyl 5-(2-chloro-4-trifluoromethylphenoxy)-2-nitrobenzoate | 2-Cl | 4-CF₃ | H | O | O | NO₂ | —CH₂CH₂— | —N(CH₃)₂ |
| 21 | 5-(N,N—Dimethylcarbamyloxy)-3-oxapentyl 5-(2-chloro-4-trifluoromethylphenoxy)-2-nitrobenzoate | 2-Cl | 4-CF₃ | H | O | O | NO₂ | —CH₂CH₂OCH₂CH₂— | —N(CH₃)₂ |

TABLE I-continued

| Ex. No. | Compound | L | M | N | X | X' | Y | R | ZR₂ |
|---|---|---|---|---|---|---|---|---|---|
| 22 | 4-(N,N—Dimethylcarbamyloxy)-2-buten-1-yl 5-(2-chloro-4-trifluoromethylphenoxy)-2-nitrobenzoate | 2-Cl | 4-CF₃ | H | O | O | NO₂ | —CH₂CH=CHCH₂— | —N(CH₃)(CH₃) |
| 23 | 4-(N,N—Dimethylcarbamyloxy) butyl 5-(2,4-dichlorophenoxy)-2-nitrobenzoate | 2-Cl | 4-Cl | H | O | O | NO₂ | —CH₂CH₂CH₂CH₂— | —N(CH₃)(CH₃) |
| 24 | 2-(N,N—Diethylcarbamyloxy) ethyl 5-(2-chloro-4-trifluoromethylphenoxy)-2-nitrobenzoate | 2-Cl | 4-CF₃ | H | O | O | NO₂ | —CH₂CH₂— | —N(CH₂CH₃)(CH₂CH₃) |
| 25 | 2-[N—(3-chlorophenyl)carbamyloxy]ethyl 5-(2-chloro-4-trifluoromethylphenoxy)-2-nitrobenzoate | 2-Cl | 4-CF₃ | H | O | O | NO₂ | —CH₂CH₂— | —NH-(3-chlorophenyl) |
| 26 | 3-Acetoxy-2,2-dimethylpropyl 5-(2-chloro-4-trifluoromethylphenoxy)-2-nitrobenzoate | 2-Cl | 4-CF₃ | H | O | O | NO₂ | —CH₂—C(CH₃)(CH₃)—CH₂— | CH₃ |
| 27 | N—[2-(Acetoxy)ethyl]-N—methyl 5-(2-chloro-4-trifluoromethylphenoxy)-2-nitrobenzamide | 2-Cl | 4-CF₃ | H | NCH₃ | O | NO₂ | CH₂CH₂ | CH₃ |
| 28 | N—[2-(Acetylthio)ethyl] 5-(2-chloro-4-trifluoromethylphenoxy)-2-nitrobenzamide | 2-Cl | 4-CF₃ | H | NH | S | NO₂ | CH₂CH₂ | CH₃ |
| 29 | 2-(N,N—Dimethylcarbamylthio) ethyl 5-(2-chloro-4-trifluoromethylphenoxy)-2-nitrobenzamide | 2-Cl | 4-CF₃ | H | NH | S | NO₂ | CH₂CH₂ | —N(CH₃)(CH₃) |
| 30 | 2-[N—(N,N—Diethylcarbamyl) amino] ethyl 5-(2-chloro-4-trifluoromethylphenoxy)-2-nitrobenzoate | 2-Cl | 4-CF₃ | H | O | NH | NO₂ | | —N(CH₂CH₃)(CH₂CH₃) |
| 31 | 2-(N—Acetylamino) ethyl 5-(2-chloro-4-trifluoromethylphenoxy)-2-nitro- | 2-Cl | 4-CF₃ | H | O | NH | NO₂ | CH₂CH₂ | CH₃ |

TABLE I-continued

| Ex. No. | Compound | L | M | N | X | X' | Y | R | ZR$_2$ |
|---|---|---|---|---|---|---|---|---|---|
| 32 | 2-(3-Cyanopropionyloxy)ethyl 5-(2-chloro-4-trifluoromethylphenoxy)-2-nitrobenzoate | 2-Cl | 4-CF$_3$ | H | O | O | NO$_2$ | —CH$_2$CH$_2$— | CH$_2$CH$_2$—CN |
| 33 | 2-(3-Chloropropionyl)ethyl 5-(2-chloro-4-trifluoromethylphenoxy)-2-nitrobenzoate | 2-Cl | 4-CF$_3$ | H | O | O | NO$_2$ | —CH$_2$CH$_2$— | CH$_2$CH$_2$Cl |
| 34 | 2-(Ethynylacetoxy)ethyl 5-(2-chloro-4-trifluoromethylphenoxy)-2-nitrobenzoate | 2-Cl | 4-CF$_3$ | H | O | O | NO$_2$ | —CH$_2$CH$_2$— | CH$_2$—C≡CH |
| 35 | 2-(3-Nitropropionyloxy)ethyl 5-(2-chloro-4-trifluoromethylphenoxy)-2-nitrobenzoate | 2-Cl | 4-CF$_3$ | H | O | O | NO$_2$ | —CH$_2$CH$_2$— | CH$_2$CH$_2$NO$_2$ |
| 36 | 2-(3,3,3-Trifluoropropionyloxy)ethyl 5-(2-chloro-4-trifluoromethylphenoxy)-2-nitrobenzoate | 2-Cl | 4-CF$_3$ | H | O | O | NO$_2$ | —CH$_2$CH$_2$— | CH$_2$CF$_3$ |
| 37 | 2-(Thiomethoxyacetoxy)ethyl 5-(2-chloro-4-trifluoromethylphenoxy)-2-nitrobenzoate | 2-Cl | 4-CF$_3$ | H | O | O | NO$_2$ | —CH$_2$CH$_2$— | CH$_2$SCH$_3$ |
| 38 | 2-[3-(N,N—Dimethylamino)propionyloxy]ethyl 5-(2-chloro-4-trifluoromethylphenoxy)-2-nitrobenzoate | 2-Cl | 4-CF$_3$ | H | O | O | NO$_2$ | —CH$_2$CH$_2$— | —CH$_2$—CH$_2$N(CH$_3$)$_2$ |
| 39 | 2-(Cyclohexylacetoxy)ethyl 5-(2-chloro-4-trifluoromethylphenoxy)-2-nitrobenzoate | 2-Cl | 4-CF$_3$ | H | O | O | NO$_2$ | —CH$_2$CH— | —CH$_2$—C$_6$H$_5$ |
| 40 | 2-(3-Hydroxypropionyloxy)ethyl 5-(2-chloro-4-trifluoromethylphenoxy)-2-nitrobenzoate | 2-Cl | 4-CF$_3$ | H | O | O | NO$_2$ | —CH$_2$CH$_2$— | CH$_2$CH$_2$OH |
| 41 | 2-(Phenylacetoxy)ethyl 5-(2-chloro-4-trifluoromethylphenoxy)-2-nitrobenzoate | 2-Cl | 4-CF$_3$ | H | O | O | NO$_2$ | —CH$_2$CH$_2$— | —CH$_2$—C$_6$H$_5$ |
| 42 | N—methyl-N—(2-acetoxyethyl)5-(2-chloro-4-trifluoromethylphenoxy)-2-nitrobenzoamide | 2-Cl | 4-CF$_3$ | H | NCH$_3$ | O | NO$_2$ | —CH$_2$—CH$_2$— | —CH$_3$ |

TABLE I-continued

| Ex. No. | Compound | L | M | N | X | X' | Y | R | ZR₂ |
|---|---|---|---|---|---|---|---|---|---|
| 43 | 3-Chloroacetoxy-2-(hydroxymethyl)propyl 5-(2-chloro-4-trifluoromethylphenoxy)-2-nitrobenzoate | 2-Cl | 4-CF₃ | H | O | O | NO₂ | —CH₂—CH—CH₂—<br>$\quad\quad\quad\;\;$ \|<br>$\quad\quad\quad\;\;$ CH₂OH | —CH₂Cl |
| 44 | 2-Chloromethyl-3-isobutynyloxypropyl 5-(2-chloro-4-trifluoromethylphenyl)-2-nitrobenzoate | 2-Cl | 4-CF₃ | H | O | O | NO₂ | —CH₂—CH—CH₂—<br>$\quad\quad\quad\;\;$ \|<br>$\quad\quad\quad\;\;$ CH₂Cl | —CH(CH₃)₂ |
| 45 | 3-Propionyloxy-2,2-(dimethyl)propyl 5-(2-chloro-4-trifluoromethylphenoxy)-2-nitrobenzoate | 2-Cl | 4-CF₃ | H | O | O | NO₂ | $\quad\quad$ CH₃<br>$\quad\quad$ \|<br>—CH₂—C—CH₂—<br>$\quad\quad$ \|<br>$\quad\quad$ CH₃ | —CH₂CH₃ |
| 46 | 2-Chloroacetoxymethyl-4-cyanobutyl 5-(2,4,6-trichlorophenoxy)-2-nitrobenzoate | 2-Cl | 4-Cl | 6-Cl | O | O | NO₂ | —CH₂—CH—CH₂—<br>$\quad\quad\quad\;\;$ \|<br>$\quad\quad\quad\;\;$ CH₂CH₂CN | —CH₂Cl |
| 47 | 3-Fluoroacetoxy-2-(methoxymethyl)propyl 5-(2,4-dichlorophenoxy)-2-nitrobenzoate | 2-Cl | 4-Cl | H | O | O | NO₂ | —CH₂—CH—CH₂—<br>$\quad\quad\quad\;\;$ \|<br>$\quad\quad\quad\;\;$ CH₂OCH₃ | —CH₂F |
| 48 | 2-(Chloroacetoxy)ethyl 2-chloro-5-(2-chloro-4-trifluoromethylphenoxy)benzoate | 2-Cl | 4-CF₃ | H | O | O | Cl | —CH₂CH₂— | —CH₂Cl |
| 49 | 2-(Chloroacetoxy)ethyl 5-(2-chloro-4-trifluoromethylphenoxy)-2-cyanobenzoate | 2-Cl | 4-CF₃ | H | O | O | CN | —CH₂—CH₂— | —CH₂Cl |
| 50 | 2-(Chloroacetoxy)ethyl-2-amino-5-(2-chloro-4-trifluoromethylphenoxy)benzoate | 2-Cl | 4-CF₃ | H | O | O | —NH₂ | —CH₂CH₂— | —CH₂Cl |
| 51 | 2-(Chloroacetoxy)ethyl 5-(2-chloro-4-trifluoromethylphenoxy)-2-(N,N-dimethylamino)benzoate | 2-Cl | 4-CF₃ | H | O | O | $\quad\quad$ CH₃<br>$\quad\;\;$ /<br>—N<br>$\quad\;\;$ \\<br>$\quad\quad$ CH₃ | —CH₂CH₂— | —CH₂Cl |
| 52 | 2-(N,N—Dimethylcarbamoylamino)ethyl 5-(2-chloro-4-trifluoromethylphenoxy)-2-nitrobenzoate | 2-Cl | 4-CF₃ | H | O | NH | NO₂ | —CH₂CH₂— | $\quad\quad$ CH₃<br>$\quad\;\;$ /<br>—N<br>$\quad\;\;$ \\<br>$\quad\quad$ CH₃ |

TABLE I-continued

| Ex. No. | Compound | L | M | N | X | X' | Y | R | ZR₂ |
|---|---|---|---|---|---|---|---|---|---|
| 53 | N—[2-(N,N—Diallylcarbamyl-oxy)ethyl] 5-(2-chloro-4-trifluoromethylphenoxy)-2-nitrobenzamide | 2-Cl | 4-CF₃ | H | NH | O | NO₂ | —CH₂CH₂— | —N(CH=CH₂)(CH=CH₂) |
| 54 | 2-[N—Methyl-N—(N,N—dimethylcarbamyl)amino] 5-(2-chloro-4-trifluoromethylphenoxy)-2-nitrobenzoate | 2-Cl | 4-CF₃ | H | O | NCH₃ | NO₃ | —CH₂CH₂— | —N(CH₃)(CH₃) |
| 55 | 2-(N,N—Dimethylcarbamyl-thio) ethyl 5-(2-chloro-4-trifluoromethylphenoxy)-2-nitrothiobenzoate | 2-Cl | 4-CF₃ | H | S | S | NO₂ | —CH₂CH₂— | —N(CH₃)(CH₃) |
| 56 | N—{2-[S—Ethylthiocarboxyamino]ethyl}-5-(2-chloro-4-(trifluoromethylphenoxy)-2-nitrobenzamide | 2-Cl | 4-CF₃ | H | NH | NH | NO₂ | —CH₂CH₂— | —S—CH₂CH₃ |
| 57 | N—[2-Ethoxycarboxyamino) ethyl] 5-(2-chloro-4-trifluoromethylphenoxy)-2-nitrobenzamide | 2-Cl | 4-CF₃ | H | NH | NH | NO₂ | —CH₂CH₂— | —OCH₂CH₃ |
| 58 | N—Methyl-N—[2-(N,N—diethyl carbamyloxy)ethyl] 5-(2-chloro-4-trifluoromethyl-phenoxy)-2-nitrobenzamide | 2-Cl | 4-CF₃ | H | NCH₃ | O | NO₂ | —CH₂CH₂— | —N(CH₂CH₃)(CH₂CH₃) |
| 59 | 2-(N,N—dimethylcarbamyl-thio)ethyl 5-(2,4,6-trichlorophenoxy)-2-nitrothiobenzoate | 2-Cl | 4-Cl | 6-Cl | S | S | NO₂ | —CH₂CH₂— | —N(CH₃)(CH₃) |
| 60 | 2-(N,N—Dimethylcarbamyl-oxy)ethyl 2-chloro-5-(2-chloro-4-trifluoromethyl-phenoxy)benzoate | 2-Cl | 4-CF₃ | H | O | O | Cl | —CH₂CH₂— | —N(CH₃)(CH₃) |
| 61 | 2-(N,N—Diethylcarbamyl-oxy)ethyl 5-(chloro-4-trifluoromethylphenoxy)-2-cyanobenzoate | 2-Cl | 4-CF₃ | H | O | O | CN | —CH₂CH₂— | —N(CH₂CH₃)(CH₂CH₃) |
| 62 | 2-(Acetylthio)ethyl 5-(2-chloro-4-trifluoromethylphenoxy)-2-nitrothiobenzoate | 2-Cl | 4-CF₃ | H | S | S | NO₂ | —CH₂CH₂— | —CH₃ |

TABLE I-continued

| Ex. No. | Compound | L | M | N | X | X' | Y | R | ZR₂ |
|---|---|---|---|---|---|---|---|---|---|
| 63 | 2-Acetoxyethyl 5-(2-chloro-4-trifluoromethylphenoxy)-2-nitrothiobenzoate | 2-Cl | 4-CF₃ | H | S | O | NO₂ | —CH₂CH₂— | —CH₃ |
| 64 | 2-(Acetylthio)ethyl 5-(2-chloro-4-trifluoromethyl-phenoxy)-2-nitrobenzoate | 2-Cl | 4-CF₃ | H | O | S | NO₂ | —CH₂CH₂— | —CH₃ |
| 65 | 2-Acetadmidoethyl 5-(2-chloro-4-trifluoromethyl-phenoxy)-2-nitrothiobenzoate | 2-Cl | 4-CF₃ | H | S | NH | NO₂ | —CH₂CH₂— | —CH₃ |
| 66 | N—[2-(Acetylthio)ethyl] 5-(2-chloro-4-trifluoro-methylphenoxy)-2-nitro-benzoamide | 2-Cl | 4-CF₃ | H | NH | S | NO₂ | —CH₂CH₂— | —CH₃ |
| 67 | N—Methyl-N—[2-(Acetylthio)ethyl]5-(2-chloro-4-tri-fluoromethylphenoxy)-2-nitrobenzoamide | 2-Cl | 4-CF₃ | H | NCH₃ | S | NO₂ | —CH₂CH₂— | —CH₃ |
| 68 | 2-(N—Methylacetamido) ethyl 5-(2-chloro-4-tri-fluoromethylphenoxy)-2-nitrobenzoate | 2-Cl | 4-CF₃ | H | S | NCH₃ | NO₂ | —CH₂CH₂— | —CH₃ |
| 69 | N—(2-Acetoxyethyl) 5-(2-chloro-4-trifluoromethyl-phenoxy)-2-nitrobenzamide | 2-Cl | 4-CF₃ | H | NH | O | NO₂ | —CH₂CH₂— | —CH₃ |
| 70 | 2-Acetamidoethyl 5-(2-chloro-4-trifluoromethyl-phenoxy)-2-nitrobenzamide | 2-Cl | 4-CF₃ | H | O | NH | NO₂ | —CH₂CH₂— | —CH₃ |
| 71 | 2-(N—methylacetamido)ethyl 5-(2-chloro-4-trifluoro-methylphenoxy)-2-nitro-benzoate | 2-Cl | 4-CF₃ | H | O | NCH₃ | NO₂ | —CH₂CH₂— | —CH₃ |
| 72 | 2-(Chloroacetoxy)ethyl 2-nitro-5-[di-(trifluoromethyl)phenoxy]benzoate | 2-CF₃ | 4-CF₃ | H | O | O | NO₂ | —CH₂CH₂— | —CH₂Cl |
| 73 | 2-Acetoxyethyl 5-(4-chloro-2-trifluorophenoxy)-2-nitrobenzoate | 2-CF₃ | 4-Cl | H | O | O | NO₂ | —CH₂CH₂— | —CH₃ |
| 74 | 2-(Chloroacetoxy) ethyl 2-nitro-5-(2-amino-4-trifluoro-methylphenoxy)benzoate | 2-NH₂ | 4-CF₃ | H | O | O | NO₂ | —CH₂CH₂— | —CH₂Cl |
| 75 | 2-(Cyclopropanecarboxythio)ethyl 5-(2-chloro-4-trifluoro-methylphenoxy)-2-nitrothio-benzoate | 2-CF₃ | 4-NO₂ | H | S | O | NO₂ | —CH₂CH₂— | △ |
| 76 | 2-(Chloroacetoxy)ethyl 5-(5-chloro-2-cyano-4-trifluoromethylphenoxy)-2-nitrobenzoate | 2-CN | 4-CF₃ | 5-Cl | O | O | NO₂ | —CH₂CH₂— | —CH₂Cl |

TABLE I-continued

| Ex. No. | Compound | L | M | N | X | X' | Y | R | ZR₂ |
|---|---|---|---|---|---|---|---|---|---|
| 77 | 2-Acetoxyethyl 5-(2-chloro-4-N,N—dimethylamino-5-methyl-phenoxy)-2-nitrobenzoate | 2-Cl | 4N(CH₃)(CH₃) | 5-CH₃ | O | O | NO₂ | —CH₂CH₂— | —CH₃ |
| 78 | 2-(Chloroacetoxy)ethyl 5-(2-chloro-4-methoxyphenoxy)-2-nitrobenzoate | 2-Cl | 4OCH₃ | H | O | O | NO₂ | —CH₂CH₂— | —CH₂Cl |
| 79 | 2-(Dichloroacetoxy)ethyl 5-(2-chloro-5-cyano-4-trifluoromethylphenoxy)-2-nitrobenzoate | 2-Cl | 4-CF₃ | CN | O | O | NO₂ | —CH₂CH₂— | —CHCl₂ |

DETAILED DESCRIPTION OF THE INVENTION

The compounds (V) of the invention are made by reacting precurser (I) with (II); or precurser (III) with (IV), as follows:

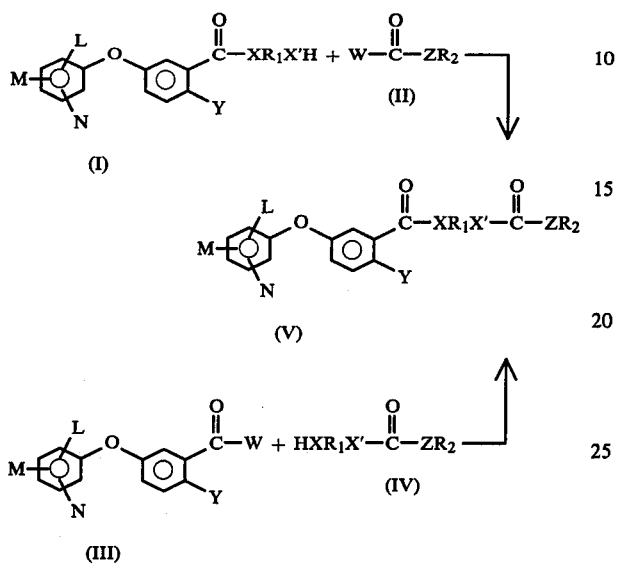

where W in (II) and (III) is chlorine or bromine; and L, M, N, Y, X, $R_1$, X', Z and $R_2$ are as defined previously. The reactions may be carried out in the presence or absence of a base, and with or without a solvent.

(I) is prepared by reacting m-phenoxybenzoic acid halide (VI) with reactant (VIII); (IV) is synthesized by reacting an acid halide,

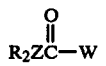

with reactant (VIII), as shown below.

These reactions

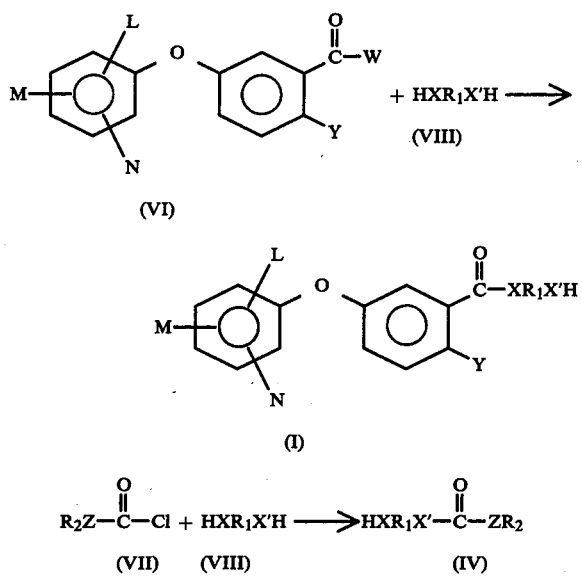

may be carried out in the presence or absence of a base, and with or without a solvent.

The X'H or XH functionality in (VIII) may be protected before condensation by reaction with a suitable protecting agent, such as chlorotrimethylsilane, which is removed later to regenerate the X'H or XH group.

The acid chloride (VI) is prepared by treating m-phenoxybenzoic acid with a chlorinating agent, such as thionyl chloride.

The ester (I, X=X'=oxygen), is also prepared from the corresponding alcohols by reaction with m-phenoxybenzoic acid (XI) in the presence of a catalyst, preferably an acid as follows:

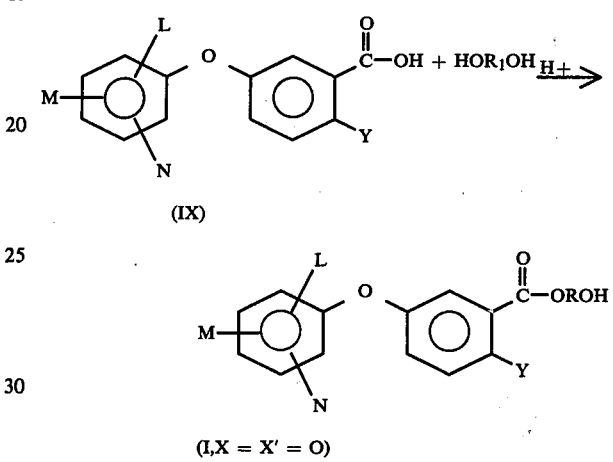

The m-phenoxybenzoic acids are readily prepared by the Ullman ether synthesis reaction between the alkali metal salt of a suitably substituted phenol with an appropriate halide.

The compounds of this invention are useful both as pre-emergent and post-emergent herbicides. Among the crops on which the compounds may be advantageously employed are, for example, soybean, rice, corn, cotton, wheat, sorghum, peanuts, safflower, beans, peas, carrots, and other cereal crops.

The phenoxybenzoates of this invention may be applied in any amount which will give the required control of weeds. A preferred rate of application of the benzoates is from 0.05 to 8 lbs. per acre. In practical application, the compounds may be applied in solid, liquid or in vaporized form, or, as it is generally done, as an active ingredient in a herbicidal composition or formulation which comprises a carrier. A generally accepted carrier is a substance which can be used to dissolve, disperse or diffuse the herbicidal components in the composition. Non-limiting examples of liquid carriers include water, organic solvents such as alcohols, ketones, halogenated hydrocarbons, aromatic hydrocarbons, ethers, amides, esters, nitriles, mineral oils and the like. Non-limiting examples of solid carriers include Kaolin, bentonite, talc, diatomaceous earth, vermiculite, clay, gypsum, grain and seed hulls, ground corn cobs and the like. In addition to a carrier, it is usually desirable to add to the composition additives such as emulsifying agents, wetting agents, binding agents, stabilizer and the like. The compounds may be formulated, for example, as a dust, wettable powders, emulsifiable concentrates, granular formulations or aerosols.

EXAMPLE 1

Preparation of 2-Chloroacetoxyethyl 5-(2-chloro-4-trifluoromethylphenoxy)-2-nitrobenzoate (A) 5-(2-chloro-4-trifluoromethylphenoxy)-2-nitro benzoyl chloride A solution of 5-(2-chloro-4-trifluoromethylphenoxy)-2-nitrobenzoic acid (448.1 g, 1.24 mole), thionyl chloride (458 g) and toluene (250 ml) was held at reflux for 8 hrs. The excess thionyl chloride and the solvent were stripped off under reduced pressure to give a reddish solid, which upon recrystallization from hexane-toluene afforded 282.9 g of the desired benzoyl chloride as a light yellow crystalline solid; mp 63°–69° C.

(B) 2-Hydroxyethyl 5-(2-chloro-4-trifluoromethylphenoxy)-2-nitrobenzoate

A well-stirred solution of 5-(2-chloro-4-(trifluoromethylphenoxy)benzoyl chloride (282.9 g, 0.74 mole) and ethylene glycol (1000 ml) was heated at 145° C. for 3 hours. Then triethylamine (30 ml) was added. The solution was reheated at 142° C. for 8 hours. After most of the ethylene glycol was distilled off under reduced pressure, the oil was taken up in 1700 ml of methylene chloride. The methylene chloride solution was washed three times with water, dried over $MgSO_4$ and concentrated to a gummy material. Molecular distillation afforded 226.2 g (75% yield) of a pale yellow gum which solidified on standing. 3.5 g of the solid was recrystallized from hexane-toluene to give 2.8 g of white solid; mp 75°–78° C.; nmr ($CDCl_3$) δ 0.3.32 (S, 1H), 3.67–4.12 (m, 2H), 4.15–4.63 (m, 2H), 7.02–8.25 (m, 6H); ir ($CHCl_3$) 1749 $Cm^{-1}$.

(C) Chloroacetyl chloride (3 g, 0.027 mole) was added dropwise to a stirred solution of 2-hydroxyethyl 5-(2-chloro-4-trifluoromethylphenoxy)-2-nitrobenzoate (8.1 g, 0.02 mole), triethylamine (2.5 g), and ether (150 ml). The heat given off during the reaction raised the temperature of the ether solution to reflux. After completion of addition, the mixture was kept at reflux for 10 min. The mixture then was allowed to cool to room temperature, poured into 200 ml of water, and 400 ml of ether was added. The ether extract was washed three times with water, dried $CaSO_4$ and concentrated to 8.6 g of yellowish oil. The oil was column chromatographed through silica gel with 20% ethyl acetate-80% hexane as eluent to afford 3.2 g of pure 2-chloroacetoxyethyl 5-(2-chloro-4-trifluoromethylphenoxy)-2-nitrobenzoate, as a pale yellow gumming material; nmr ($CDCl_3$) δ 4.16 (S, 2H), 4.50 (S, 4H), 6.98–8.18 (m, 6H); ir ($CHCl_3$) 1752, 1765.

EXAMPLES 2 THROUGH 15

The following compounds within the scope of this invention were prepared using procedures similar to that described in Example 1.

(2) 2-Acetoxyethyl 5-(2-chloro-4-trifluoromethylphenoxy)-2-nitrobenzoate; nmr ($CDCl_3$) δ 2.06 (S, 3H), 4.47 (m, 4H), 7.02–7.89 (m, 6H); ir ($CHCl_3$) 1743, 1780 $Cm^{-1}$.

(3) 2-(Isobutyryloxy)ethyl 5-(2-chloro-4-trifluoroethylphenoxy)-2-nitrobenzoate; nmr ($CDCl_3$) δ 1.13 (d, 6H), 2.58 (sept, 1H), 4.52 (m, 4H), 7.02–8.21 (m, 6H); ir ($CHCl_3$) 1743, 1750 $Cm^{-1}$.

(4) 2-(Cyclopropanecarboxy)ethyl 5-(2-chloro-4-trifluoromethyl phenoxy)-2-nitrobenzoate; ($CDCl_3$) δ 0.58–1.89 (m, 5H), 4.46 (m, 4H), 7.00–8.25 (m, 6H); ir ($CHCl_3$) 1740, 1749 $Cm^{-1}$.

(5) 2-(Acryloyloxy)ethyl 5-(2-chloro-4-trifluoromethylphenoxy)-2-nitrobenzoate; nmr ($CDCl_3$) δ 4.54 (m, 4H), 4.72–6.77 (m, 3H), 7.05–8.24 (m, 6H); ir ($CHCl_3$) 1747, 1753 $Cm^{-1}$.

(6) 2-(Methoxyacetoxy)ethyl 5-(2-chloro-4-trifluoromethylphenoxy)-2-nitrobenzoate; nmr ($CDCl_3$) δ 3.42 (s, 3H), 4.06 (s, 2H), 4.50 (s, 4H), 6.79–8.23 (m, 6H); ir ($CHCl_3$) 1750 $Cm^{-1}$.

(7) 3-Acetoxypropyl 5-(2-chloro-4-trifluoromethylphenoxy)-2-nitrobenzoate; nmr ($CDCl_3$) δ 2.17 (s, 3H), 2.00 (t, 2H), 2.60 (t, 2H), 4.35 (t, 2H), 7.03–8.23 (m, 6H); ir ($CHCl_3$) 1730, 1750 $Cm^{-1}$.

(8) 4-(Chloroacetoxy)butyl 5-(2-chloro-4-trifluoromethylphenoxy)-2-nitrobenzoate; nmr ($CDCl_3$) δ 1.78 (t, 2H), 1.89 (t, 2H), 4.07 (s, 3H), 4.05–4.58 (m, 4H), 6.94–8.20 (m, 6H); ir ($CHCl_3$) 1747, 1733 $Cm^{-1}$.

(9) 2-(3-Chlorobenzoyloxy)ethyl 5-(2-chloro-4-trifluoromethylphenoxy)-2-nitrobenzoate; nmr ($CDCl_3$) δ 4.66 (s, 4H), 6.98–8.24 (m, OH); ir ($CHCl_3$) 1738, 1750 $Cm^{-1}$.

(10) 2-(2,4-Dichlorobenzoyloxy)ethyl 5-(2-chloro-4-trifluoromethyl phenoxy)-2-nitrobenzoate; nmr ($CDCl_3$) δ 4.66 (s, 4H), 6.70–8.62 (m, 9H); ir ($CH_3CN$) 1748 $Cm^{-1}$.

(11) 4-Acetoxy-2-buten-1-yl 5-(2-chloro-4-trifluoromethylphenoxy)-2-nitrobenzoate; nmr ($CDCl_3$) δ 2.06 (s, 3H), 4.73 (d, 2H), 4.98 (d, 2H), 5.87 (t, 2H), 7.00–8.24 (m, 6H); ir ($CHCl_3$) 1743 $Cm^{-1}$.

(12) 11-Chloroacetoxy-3,6,9-trioxaundecyl 5-(2-chloro-4-trifluoromethylphenoxy)-2-nitrobenzoate; nmr ($CDCl_3$) δ 3.32–4.62 (m, 18H), 7.92–8.20 (m, 6H); ir ($CHCl_3$) 1752, 1738 $Cm^{-1}$.

(13) 2-Benzoyloxyethyl 5-(2-chloro-4-trifluoromethylphenoxy)-2-nitrobenzoate; nmr ($CDCl_3$) δ 4.66 (s, 4H), 6.96–8.30 (m, 11H); ir ($CHCl_3$) 1735, 1750 $Cm^{-1}$.

(14) 6-Acetoxy-3,4-dithiahexyl 5-(2-chloro-4-trifluoromethylphenoxy)-2-nitrobenzoate; nmr ($CDCl_3$) δ 2.07 (s, 3H), 2.98 (q, 4H), 4.23 (t, 2H), 4.58 (t, 2H), 6.98–8.22 (m, 6H); ir ($CHCl_3$) 1748 $Cm^{-1}$.

(15) 2-(3-Amino-2,5-dichlorobenzoyloxy)ethyl 5-(2-chloro-4-trifluoromethylphenoxy)2-nitrobenzoate; nmr ($DMSO-Cl_6$) δ 4.60 (s, 4H), 5.91 (s, 2H), 6.82–8.32 (m, 8H); ir (neat) 3495, 3400, 1742 $Cm^{-1}$.

EXAMPLE 16

Preparation of 2-Propionyloxyethyl 5-(2-chloro-4-trifluoromethylphenoxy)-2-nitrobenzoate Propionyl chloride (2.9 g, 0.032 mole) was added dropwise to a solution of 2-hydroxy 5-(2-chloro-4-trifluoromethylphenoxy)-2-nitrobenzoate (6 g, 0.0016 mole) and triethylamine (25 ml). A yellowish salt was precipitated. The mixture then was heated to and held for 1.75 hr. at reflux, cooled and taken into 400 ml of methylene chloride. The methylene chloride solution was washed two times with water, dried over $MgSO_4$ and concentrated to an oil. Kugelrohr distillation at a temperature 170° C. afforded 5.7 g (91% yield) of colorless gum; nmr ($CDCl_3$) δ 1.09 (t, 3H), 2.37 (q, 2H), 4.45 (m, 4H), 7.00–8.22 (m, 6H); ir ($CHCl_3$) 1750 $Cm^{-1}$.

EXAMPLE 17

Preparation of 2-(Trifluoroacetoxy)ethyl 5-(2-chloro-4-trifluoromethylphenoxy)-2-nitrobenzoate Trifluoroacetic anhydride (8.4 g, 0.04 mole) was added portionwise to a solution of 2-hydroxyethyl 5-(2- chloro-4-trifluoromethylphenoxy)-2-nitrobenzoate (7 g, 0.017 mole) and 50 ml of ether. After holding at 30°-35° C. for an hour, the solution was allowed to stand at room temperature overnight. Excess trifluoroacetic anhydride was removed and 300 ml of ether was added. The ethereal solution was washed three times with water, dried over CaSO$_4$ and concentrated to an oil. Kugelrohr distillation afforded 3.6 g of pure 2-(trifluoroacetoxy)ethyl 5-(2-chloro-4-trifluoromethylphenoxy)-2-nitrobenzoate as a gumming material (yield: 42.2%); nmr (CDCl$_3$) δ 4.62 (s, 4H), 7.02-8.19 (m, 6H); ir (CHCl$_3$) 1752, 1803 Cm$^{-1}$.

EXAMPLE 18

Preparation of 5-(chloroacetoxy)-3-oxapentyl 5-(2-chloro-4-trifluoromethylphenoxy)-2-nitrobenzoate (A) 5-Hydroxy-3-oxapentyl 5-(2-chloro-4-trifluoromethylphenoxy)-2-nitrobenzoate A mixture of 5-(2-chloro-4-trifluoromethylphenoxy)-2-nitrobenzoic acid (5.6 g, 0.015 mole), 2-hydroxyethyl ether (6.4 g, 0.06 mole) and p-toluenesulfonic acid (200 mg) was heated at 135°-142° C. for 26 hrs. The resulting solution was cooled to room temperature, taken into 400 ml of ether. The ethereal solution was washed three times with water, dried over CaSO$_4$ and concentrated to 4.9 g of a yellowish gum. The gum was chromatographed on silica gel and eluted with hexane-ethyl acetate (90:10); yield 3.4 g of pure 5-hydroxy-3-oxapentyl 5-(2-chloro-4-trifluoromethylphenoxy)-2-nitrobenzoate as a pale yellow gum; nmr (DMSO-d$_6$) δ 3.56 (s, broad 5H), 3.76 (m, 2H), 4.52 (m, 2H), 7.18-8.40 (m, 6H); ir (CHCl$_3$) 3610, 1750 Cm$^{-1}$.

(B) 5-Hydroxy-3-oxapentyl 5-(2-chloro-4-trifluoromethylphenoxy)-2-nitrobenzoate (4 g, 0.009 mole) and triethylamine (2 ml) were dissolved in 200 ml of anhydrous ether in a 500 ml round-bottomed flask. Chloroacetyl chloride (5 g, 0.44 mole) was added dropwise. The solution was held at reflux for 4.5 hrs. A large amount of salt precipitated. The ether solution was washed two times with sodium bicarbonate and three times of water, dried over CaSO$_4$ and concentrated to 3.6 g 5-(chloroacetoxy)3-oxapentyl 5-(2-chloro-4-trifluoromethylphenoxy)-2-nitrobenzoate as a gum; nmr (CDCl$_3$) δ 3.62-3.93 (m, 4H), 4.09 (s, 3H), 4.27-4.66 (m, 4H), 6.96-8.22 (m, 6H); ir (CHCl$_3$) 1754, 1768 Cm$^{-1}$.

EXAMPLE 19

Preparation of 6-(N,N-dimethylcarbamyloxy hexyl-5-(2-chloro-4-trifluoromethylphenoxy)-2-nitrobenzoate 6-Hydroxyethyl 5-(2-chloro-4-trifluoromethylphenoxy)-2-nitrobenzoate (5 g, 0.014 mole) and N,N-dimethylcarbamyl chloride (11.68 g, 0.109 mole) were charged into a 80 ml round-bottomed flask. The solution was heated at 100° C. for 2 hrs, cooled and take into 300 ml of ether. The ethereal solution was washed three times with water, dried over MgSO$_4$. After the solvent being stripped off 5.9 g of 6-(N,N-dimethyl carbamyloxy)hexyl 5-(2-chloro-4-trifluoromethylphenoxy)-2-nitrobenzoate was obtained as a brownish gum (yield: 86%); nmr (CDCl$_3$) δ 1.06-2.08 (m, 8H), 2.90 (s, 6H), 4.09 (t, 2H), 4.30 (t, 2H), 6.98-8.21 (m, 6H); ir (CHCl$_3$) 1696, 1742 Cm$^{-1}$.

EXAMPLES 20 THROUGH 25

The following compounds within the scope of this invention were prepared using procedures similar to that described in Example 19.

(20) 2-(N,N-Dimethylcarbamyloxy)ethyl 5-(2-chloro-4-trifluoromethylphenoxy)-2-nitrobenzoate; nmr δ (DMSO-d$_6$) 2.86 (s, 6H), 4.20-4.76 (m, 4H), 7.22-8.29 (m, 6H); ir (CHCl$_3$) 1702, 1748 Cm$^{-1}$.

(21) 5-(N,N-Dimethylcarbamyloxy-3-oxapentyl 5-(2-chloro-4-trifluoromethylphenoxy)-2-nitrobenzoate; nmr (CDCl$_3$) δ 2.92 (s, 6H), 3.72 (m, 4H), 4.20 (m, 2H), 4.50 (m, 2H), 7.00-8.26 (m, 6H); ir (CHCl$_3$) 1700, 1746 Cm$^{-1}$.

(22) 4-(N,N-Dimethylcarbamyloxy-2-buten-1-yl 5-(2-chloro-4-trifluoromethylphenoxy)-2-nitrobenzoate; nmr (CDCl$_3$) δ 2.92 (s, 6H), 4.72 (m, 2H), 4.98 (m, 2H), 5.86 (m, 4H), 7.00-8.22 (m, 6H); ir (CHCl$_3$) 1750, 1710, 1594 Cm$^{-1}$.

(23) 4-(N,N-Dimethylcarbamyloxy)butyl 5-(2,4-dichlorophenoxy)-2-nitrobenzoate; nmr (CDCl$_3$) δ 1.54-2.06 (m, 4H) 2.92 (s, 6H), 3.93-4.56 (m, 4H), 6.95-8.19 (m, 6H); ir (CHCl$_3$) 1702, 1748 Cm$^{-1}$.

(24) 2-(N,N-Diethylcarbamyloxy)ethyl 5-(2-chloro-4-trifluoromethylphenoxy)-2-nitrobenzoate; nmr (CDCl$_3$) δ 110 (t, 6H), 3.28 (q, 4H), 4.49 (m, 4H), 6.98-8.23 (m, 6H); ir (CHCl$_3$) 1720, 1760 Cm$^{-1}$.

(25) 2-[N-(3-chlorophenyl)carbamyloxy]ethyl 5-(2-chloro-4-trifluoromethylphenoxy)-2-nitrobenzoate; nmr (DMSO-d$_6$) 4.16-4.88 (m, 4H), 6.86-8.42 (m, 10H); ir (CHCl$_3$) 3245, 1604, 1750 Cm$^{-1}$.

EXAMPLE 26

Preparation of 3-Acetoxy-2,2-dimethylpropyl 5-(2-chloro-4-trifluoromethylphenoxy)-2-nitrobenzoate (A) 3-hydroxy-2,2-dimethyl-propyl 5-(2-chloro-4-trifluoromethylphenoxy)-2-nitrobenzoate In a three-necked 250 ml round-bottomed flask, sodium hydride (1.6 g, 60/40% in oil, 0.04 mole) was washed two times with hexane and pre-dried THF (100 ml) was added. 1,3-propandiol (27.4 g, 0.26 mole) then was added dropwise and the mixture was stirred for an hour at room temperature. {5-[2-chloro-4-(trifluoromethyl)phenoxy]-2-nitro} benzoyl chloride (10 g, 0.026 mole) was added in ½ hr. at a temperature below 30° C. The mixture was heated to 57° for 1.25 hr., cooled, and concentrated under vacuum. The mixture then was taken up in 500 ml of ether, washed three times with water, dried over MgSO$_4$ and concentrated to an oil, Kugelrohr distillation of the oil afforded 5.35 g of the hydroxypropanyl ester. Purification of the oil through a silica gel column with 65% hexane—35% ethyl acetate as an eluent gave 3.5 g of the pure 3-hydroxy-2,2-dimethyl-propyl 5-(2-chloro-4-trifluoromethylphenoxy)-2-nitro benzoate; nmr (CDCl$_3$) δ 0.96 (s, 6H), 2.48 (s, 1H), 3.40 (s, 2H), 4.15 (s, 2H), 7.05-8.22 (m, 6H); ir (CHCl$_3$) 3650, 1744 Cm$^{-1}$.

(B) Acetyl chloride (0.79 g, 0.01 mole) was added to a solution of 3-hydroxy-2,2-dimethyl-propyl 5-(2-chloro-4-trifluoromethylphenoxy)-2-nitrobenzoate (0.25 g, 0.00056 mole) and THF (10 ml). The solution was held at reflux for 3 hrs., cooled and concentrated. The residue was taken into 250 ml of ether, washed two times with water and dried over MgSO$_4$. After the solvent was stripped off, 2.1 g of 3-Acetoxy-2,2-dimethylpropyl 5-(2-chloro-4-trifluoromethylphenoxy)-2-nitrobenzoate was obtained as a yellowish gum, nmr (CDCl$_3$) δ 1.0 (s, 6H), 2.03 (s, 3H), 3.87 (s, 2H), 4.12 (s, 2H), 6.96–8.22 (m, 6H); ir (CHCl$_3$) 1743 Cm$^{-1}$.

EXAMPLE 27

Preparation of N-[2-(Acetoxy)ethyl]-N-methyl 5-(2-chloro-4-trifluoromethylphenoxy)-2-nitrobenzamide (A) N-(2-Hydroxyethyl)-N-methyl 5-(2-chloro-4-trifluoromethylphenoxy)-2-nitrobenzamide 5-(2-chloro-4-trifluoromethylphenoxy)-2-nitrobenzoyl chloride (7 g, 0.0184 mole) was added over 1 hr to a solution of N-methylaminoethanol (2.8 g, 0.0372 mole), triethylamine (3.7 g, 0.0368 mole) and THF (30 ml) at 25°–38°. The resulting mixture was heated to and held at reflux for 1.5 hrs., cooled and concentrated. The residue was taken into 400 ml of ether, washed three times with water, dried over MgSO$_4$ and concentrated to 7.8 g of crude product. Kugelrohr distillation under reduced pressure afforded 3.0 g of pure N-(2-Hydroxyethyl)-N-methyl 5-(2-chloro-4-trifluoromethylphenoxy)-2-nitrobenzamide as a gum; nmr (CDCl$_3$) δ 2.95–3.08 (2S, 3H); 3.22–3.82 (m) 4.74 (s, 1H), 7.04–8.52 (m, 6H); ir (CHCl$_3$) 3640, 3420, 1648 Cm$^{-1}$.

(B) Acetyl chloride (2.7 g, 0.0344 mole) was added dropwise in 5 mins. to a solution of N-(2-hydroxyethyl)-N-methyl 5-(2-chloro-4-trifluoromethylphenoxy)-2-nitrobenzamide (7.2 g, 0.0172 mole), triethylamine (25 ml) and THF (25 ml). The resulting mixture was heated up to and held at reflux for 2.5 hrs., cooled and concentrated. The residue was taken into 500 ml of ether, washed two times with water, dried over MgSO$_4$ and concentrated to 8.6 g of crude product. The crude product was purified on a column of silica gel using ethyl acetate cyclohexane (1:3) as eluent to yield 3.5 g of pure N-[2-(acetoxy)ethyl]-N-methyl 5-(2-chloro-4-trifluoromethylphenoxy)-2-nitrobenzamide as a gum; nmr (CDCl$_3$) δ 2.04 (s, 3H), 2.92 (s)—3.15 (s) (3H), 3.40 (t)—3.79 (t) (2H); 4.12 (t)—4.40 (t) (2H), 6.80–8.42 (m, 6H); ir (CHCl$_3$) 1750, 1655 Cm$^{-1}$.

EXAMPLE 28

Preparation of N-[2-(Acetylthio)ethyl] 5-(2-chloro-4-trifluoromethylphenoxy)-2-nitrobenzamide (A) N-(2-Thioethyl) 5-(2-chloro-4-trifluoromethylphenoxy)-2-nitrobenzamide 2-Aminoethanethiol hydrochloride (5.7 g, 0.050 mole) was placed in a 3-neck 100 ml round-bottom flask with rubber septum, magnetic stirrer, gas inlet and outlet valves. Acetonitrile (50 ml) and diisopropylethylamine (19.0 ml, 0.11 mole) were introduced under nitrogen. The resulting suspension was chilled to 0° C. and chlorotrimethylsilane (7.0 ml, 0.055 mole) was added at once with a 10 c.c. syringe. After 20 mins., 5-(2-chloro-4-trifluoromethylphenoxy)-2-nitrobenzoyl chloride (19.0 g, 0.050 mole) in 20 ml of acetonitrile was added dropwise over 0.5 hr. Diisopropylethylamine (8.7 ml, 0.050 mole) was added and the mixture was stirred at 0° for 1 hr. and at room temperature for 3 hrs. The mixture was poured into ice/water (150 ml), extracted with dichloromethane (2×75 ml). The extract was washed with water (2×50 ml), 5% hydrochloric acid (1×50 ml), 5% sodium bicarbonate (1×75 ml) and saturated sodium chloride solution (1×75 ml). After drying over sodium sulfate, the solvent was removed in vacuo to yield 19.5 g of N-(2-thioethyl) 5-(2-chloro-4-trifluoromethylphenoxy)-2-nitrobenzamide as a brown solid; m.p. (129°–132° C.); nmr (CDCl$_3$) δ1.44 (t, 1H), 2.78 (q, 2H), 3.53 (q, 2H), 6.38–8.28 (m, 7H); ir (CHCl$_3$) 3452, 3320, 1675 Cm$^{-1}$.

(B) Acetyl chloride (2.1 ml, 0.038 mole) was added dropwise into a solution of N-(2-thioethyl) 5-(2-chloro-4-trifluoromethylphenoxy)-2-nitrobenzamide (5 g, 0.012 mole), triethylamine (5 ml) and acetonitrile (100 ml) at 0° C. The resulting mixture was stirred for 5 hrs. and poured into 300 ml of ether. The ether solution was washed three times with water, dried over CaSO$_4$ and concentrated to 4.7 g of orange gum. Kugelrohr distillation at 160° C. and 1.5 mm Hg afforded 3.5 g of pure N-[2-(acetylthio)ethyl]5-(2-chloro-4-trifluoromethylphenoxy)-2-nitrobenzamide; nmr (CDCl$_3$) δ2.32 (s, 3H), 3.13 (m, 2H), 3.60 (m, 2H), 652 (s, broad, 1H), 6.89–8.20 (m, 6H); ir (CHCl$_3$) 3460, 3360, 1682, 1592 Cm$^{-1}$.

EXAMPLE 29

Preparation of 2-(N,N-Dimethylcarbamylthio)ethyl 5-(2-chloro-4-trifluoromethylphenoxy)-2-nitrobenzamide N,N-Dimethylcarbamyl chloride (4 g, 0.037 mole) was added dropwise to a solution of N-(2-thioethyl) 5-(2-chloro-4-trifluoromethylphenoxy)-2-nitrobenzamide (5 g, 0.012 mole), triethylamine (5 ml) and acetonitrile (100 ml) at 0° C. After being stirred at 0° C. for 5.5 hrs. the solvent was stripped off under reduced pressure. The residue was taken into 400 ml of ether, washed three times with water, dried over CaSO$_4$ and concentrated to 6.2 g of yellow solid. The crude solid was chromatographed through a silica gel column (ethyl acetate: cyclohexane, 3:7), to give 4.2 g of pure 2-(N,N-dimethylcarbamylthio)ethyl 5-(2-chloro-4-trifluoromethylphenoxy)-2-nitrobenzamide as a yellowish white solid; mp 101°–102° C., nmr (CDCl$_3$) 2.95 (s, 6H), 3.10 (m, 2H), 3.63 (m, 2H), 6.80–8.24 (m, 6H); ir (CHCl$_3$) 3450, 3320, 1675, 1650 Cm$^{-1}$.

EXAMPLE 30

Preparation of 2-[N-(N,N-Diethylcarbamyl)amino]ethyl 5-(2-chloro-4-trifluoromethylphenoxy)-2-nitrobenzoate (A) N,N-Diethyl-N'-hydroxyethyl urea N,N-Diethylcarbamyl chloride (8.2 g, 0.06 mole) in THF (15 ml) was added dropwise to a solution of aminoethanol (3.08 g, 0.05 mole), triethylamine (6.08 g, 0.06 mole) and THF (25 ml) at 0° C. The mixture was stirred at room temperature for 60 hrs., filtered and concentrated to 9.0 g of N,N-diethyl-N'-hydroxyethyl urea as a pale yellow oil; nmr (CDCl$_3$) δ1.15 (t, 3H), 2.88–3.84 (m, 8H), 5.26 (s, broad, 1H), ir (neat) 3380, 1620 Cm$^{-1}$.

(B) 5-(2-chloro-4-trifluoromethylphenoxy)-2-nitrobenzoyl chloride (3.8 g, 0.010 mole) in 15 ml of THF was added dropwise to a solution of N,N-diethyl-N'-hydroxyethyl urea (2.5 g, 0.015 mole), triethylamine (1.2 g, 0.012 mole) and THF (25 ml) at 0° C. The resulting mixture was stirred at room temperature overnight, filtered and concentrated. The residue was taken into 75 ml of methylene chloride, washed three times with a saturated NaHCO$_3$ solution and one time with water. After being dried over Na$_2$SO$_4$ and concentrated, a brown oil (5.0 g) was afforded. The oil was column chromatographed through silica gel with 50% ethyl acetate-50% cyclohexane as eluent to give 3.3 g of 2-[N-(N,N-diethylcarbamyl)amino]ethyl 5-(2-chloro-4-trifluoromethylphenoxy)-2-nitrobenzoate as a brown solid; mp 89°–90° C.; NMR (CDCl$_3$) δ1.12 (t, 6H), 3.23 (q, 4H), 3.67 (t, 2H), 4.46 (t, 2H), 4.95 (s, broad 1H), 6.92–8.28 (m, 6H); ir (CHCl$_3$) 3485, 1750, 1680 Cm$^{-1}$.

EXAMPLE 31

Preparation of 2-(N-Acetylamino)ethyl 5-(2-chloro-4-trifluoromethylphenoxy)-2-nitrobenzoate N-Acetylethanolamine (2.9 g, 0.021 mole, 75% by wt. in H$_2$O) and toluene (60 ml) were introduced in a 100 ml round-bottom flask equipped with a Dean-Stark apparatus. The mixture was held at reflux for 2 hrs. to remove water from the solution. An oil separated from the toluene solution upon cooling. THF (50 ml) was added. To the resulting solution were added 5-(2-chloro-4-trifluoromethylphenoxy)(-2-nitrobenzoyl chloride) (8 g, 0.021 mole) and triethylamine (1 ml). The mixture was held at reflux for 1.67 hr. and concentrated. The residue was taken into 450 ml of ether, washed two times with H$_2$O, dried over MgSO$_4$, filtered and concentrated to yield 8.0 g of gum. The gum was column chromatographed through silica gel with 20% ethyl acetate-80% cyclohexane as eluent to give 6.4 g of 2-(N-acetylamino)ethyl 5-(2-chloro-4-trifluoromethylphenoxy)-2-nitrobenzoate as a brownish gum nmr (CDCl$_3$) δ1.98 (s, 3H), 3.58 (m, 2H), 4.42 (m, 2H), 6.25 (s, broad 1H), 6.98–8.22 (m, 6H); ir (CHCl$_3$) 3464, 1752, 1680 Cm$^{-1}$.

EXAMPLE 32

Herbicidal Tests

Tests were made on two flats seeded with species of representative monocotyledonous and dicotyledonous plants. The test chemical was applied to one such flat immediately after it was seeded. The other flat contained plants on which the first true leaves had developed before the chemical was applied. The response was rated 12 to 21 days after treatment on a scale of 0 to 9 where 0 represents no injury and 9 represents complete kill.

The results are shown in the following tables:

TABLE II

Herbicidal Effectiveness of Post-Emergence Application (At 10 lbs./acre)

| Ex. No. | MNGY | MSTD | FOX | JPN | CRB | PIG |
|---|---|---|---|---|---|---|
| 1 | 9 | 9 | 6 | 2 | 5 | 9 |
| 2 | 9 | 9 | 9 | 9 | 9 | 9 |
| 3 | 9 | 9 | 9 | 8 | 8 | 9 |
| 4 | 9 | 9 | 9 | 7 | 9 | 9 |
| 5 | 9 | 9 | 8 | 6 | 7 | 9 |
| 6** | 9 | 9 | 5 | 3 | 6 | 9 |
| 7 | 9 | 9 | 9 | 6 | 9 | 9 |
| 8 | 9 | 9 | 9 | 8 | 9 | 9 |
| 9 | 6 | 7 | 6 | 5 | 4 | 9 |
| 10 | 5 | 6 | 3 | 3 | 2 | 9 |
| 11** | 9 | 9 | 4 | 2 | 5 | 9 |
| 12 | 9 | 9 | 9 | 8 | 9 | 9 |
| 13 | 7 | 8 | 8 | 5 | 7 | 9 |
| 14 | 6 | 9 | 7 | 4 | 8 | 9 |
| 15 | 5$^N$ | 7$^N$ | 8$^N$ | 6$^N$ | 5$^N$ | 8$^N$ |
| 16 | 9 | 9 | 9 | 9 | 9 | 9 |
| 17 | 9 | 9 | 9 | 7 | 8 | 9 |
| 18 | 9 | 9 | 9 | 5 | 8 | 9 |
| 19 | 6 | 9 | 9 | 8 | 9 | 9 |
| 20 | 9 | 9 | 9 | 8 | 9 | 9 |
| 21 | 9 | 9 | 9 | 5 | 7 | 9 |

TABLE II-continued

Herbicidal Effectiveness of Post-Emergence Application (At 10 lbs./acre)

| Ex. No. | MNGY | MSTD | FOX | JPN | CRB | PIG |
|---|---|---|---|---|---|---|
| 22 | 8 | 9 | 8 | 4 | 5 | 9 |

*Rated on scale of 0 to 9, from no visible effect on foliage to 100% destruction; with N = Necrosis; MNGY = morning glory, MSTD = mustard, FOX = yellow foxtail, JPN = Japanese millet, CRB = crabgrass, PIG = pigweed.
**application rate 1.2 lbs./acre

TABLE III

Herbicidal Effectiveness of Pre-Emergence Application (At 10 lbs./acre)

| Ex. No. | MNGY | MSTD | FOX | JPN | CRB | PIG |
|---|---|---|---|---|---|---|
| 1 | 9 | 9 | 9 | 9 | 9 | 9 |
| 2 | 9 | 9 | 9 | 9 | 9 | 9 |
| 3 | 9 | 9 | 9 | 8 | 9 | 9 |
| 4 | 9 | 9 | 9 | 9 | 9 | 9 |
| 5 | 8 | 9 | 7 | 5 | 9 | 9 |
| 6** | 9 | 9 | 6 | 5 | 9 | 9 |
| 7 | 9 | 9 | 9 | 9 | 9 | 9 |
| 8 | 9 | 9 | 9 | 8 | 9 | 9 |
| 9 | 7 | 9 | 8 | 2 | 8 | 9 |
| 10 | 5 | 9 | 9 | 7 | 8 | 9 |
| 12 | 9 | 9 | 9 | 7 | 9 | 9 |
| 13 | 9 | 9 | 9 | 6 | 9 | 9 |
| 14 | 7 | 9 | 9 | 6 | 9 | 9 |
| 15 | 4$^F$ | 7$^{S+,F}$ | 8 | 3$^C$ | 8 | 9 |
| 16 | 9 | 9 | 9 | 9 | 9 | 9 |
| 17 | 9 | 9 | 9 | 9 | 9 | 9 |
| 18 | 9 | 9 | 9 | 9 | 9 | 9 |
| 19 | 9 | 9 | 9 | 8 | 9 | 9 |
| 20 | 9 | 9 | 9 | 9 | 9 | 9 |
| 21 | 5 | 9 | 8 | 6 | 9 | 9 |
| 22 | 9 | 9 | 6 | 8 | 9 | 9 |

*Rated on scale of 0 to 9, from no visible effect on foliage to 100% destruction; with S = moderate stunting, $S+$ = severe stunting, $C$ = chlorosis, $F$ = formative; MNGY = morning glory, MSTD = mustard, FOX = yellow foxtail, JPN = Japanese millet, CRB = crabgrass, PIG = pigweed.
**application rate 1.2 lbs./acre In summary, the compounds of this invention show high pre- and post-emergence herbicidal activity against indicator weeds, and are particularly effective against broadleaf weeds, such as morning glory. In addition to such effective herbicidal activity, they exhibit an unusual selectivity against important agromonic crops, such as cotton, rice and soybean.

While the invention has been described with particular reference to certain embodiments thereof, it will be understood that certain modifications and changes may be made which are within the skill of the art. Therefore it is intended to be bound only by the appended claims.

What is claimed is:
1. A compound of the formula

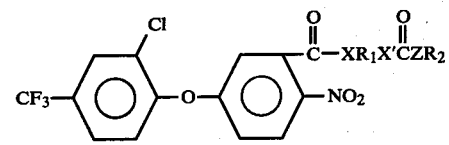

where:
X and X' are independently oxygen, sulfur, disulfur, or —NR$_5$;
R$_1$ is a saturated or unsaturated, straight or branched chain aliphatic diradical C$_1$–C$_{18}$ wherein one or more of the methylene group may be replaced by oxygen, sulfur, —SO—, —SO$_2$—, or —NR$_6$; where the aliphatic diradical may be optionally substituted with halogen, trihalomethyl, cyano, hydroxy, alkoxy, aryl, cyano or a cyclic alkyl $C_3$-$C_6$;

Z is oxygen, sulfur, $NR_7$, or a direct bond;

$R_2$ is a saturated straight or branched chain aliphatic hydrocarbon radical $C_1$-$C_8$ substituted with halogen, trihalomethyl, cyano, nitro, hydroxy, alkoxy, thioalkoxy or aryl; an aryl radical optionally substituted with halogen, trihalomethyl, cyano, nitro, alkyl, alkoxy or hydroxy; a cyclic alkylene or alkenylene ring $C_3$-$C_6$ optionally substituted with halogen, trihalomethyl, hydroxy, alkyl, alkoxy or cyano; or $R_2$ can be isopropyl when $R_1$ is —$CH_2CH(CH_2Cl)CH_2$—; ethenyl or acetoxy when X is —NH—; ethyl when X is —$N(CH_3)$— or methyl when $R_1$ is —$C_2H_3$=$C_2H_3$—, —$C_2H_4SSC_2H_4$—, or when X is —$N(CH_3)$—, —NH— or —S— or when X' is —NH—, —S— or —$N(CH_3)$—;

$R_3$, $R_4$, $R_5$, $R_6$, and $R_7$, and are independently hydrogen, a saturated or unsaturated, straight or branched chain aliphatic radical $C_1$-$C_8$ optionally substituted with halogen, hydroxy, alkoxy, cyano or nitro.

2. A compound according to claim 1 wherein $R_1$ is an alkylene diradical $C_1$-$C_{18}$.

3. A compound according to claim 1 wherein $R_1$ is an alkylene diradical $C_1$-$C_{18}$ wherein one or more of the alkylene group is replaced by oxygen, sulfur, disulfur, —SO—, —$SO_2$—, or —$NR_6$.

4. A compound according to claim 1 wherein Z is a direct bond.

5. A compound according to claim 1 wherein Z is a $NR_7$ group wherein $R_7$ is an alkylene radical $C_1$-$C_4$.

6. A compound according to claim 1 wherein $R_2$ is a saturated aliphatic radical $C_1$-$C_4$.

7. A compound according to claim 1 wherein $R_2$ is an unsaturated aliphatic radical $C_2$-$C_4$.

8. A compound according to claim 1 wherein $R_2$ is a saturated aliphatic radical $C_1$-$C_4$ substituted with halogen.

9. A compound according to claim 1 wherein both X and X' are oxygen.

10. A compound according to claim 1 which is 2-(chloroacetoxy)ethyl 5-(2-chloro-4-trifluoromethylphenoxy)-2-nitrobenzoate.

11. A compound according to claim 1 which is 2-(propionyloxy)ethyl 5-(2-chloro-4-trifluoromethylphenoxy)-2-nitrobenzoate.

12. A compound according to claim 1 which is 2-(trifluoroacetoxy)ethyl 5-(2-chloro-4-trifluoromethylphenoxy)-2-nitrobenzoate.

13. A compound according to claim 1 which is 2-(methoxyacetoxy)-ethyl 5-(2-chloro-4-trifuoromethylphenoxy)-2-nitrobenzoate.

14. A herbicidal composition comprising an effective amount of a compound of the formula of claim 1, and an agronomically acceptable carrier.

15. A composition according to claim 14 wherein $R_2$ is an alkylene diradical $C_1$-$C_{18}$ wherein one or more of the methylene group may be replaced by oxygen, sulfur, disulfur, —SO—, —$SO_2$—, or —$NR_6$; Z is a direct bond, or $NR_7$ where $R_7$ is alkyl $C_1$-$C_4$, $R_2$ is a saturated aliphatic radical $C_1$-$C_4$, an unsaturated aliphatic radical $C_2$-$C_4$ or a saturated aliphatic radical $C_1$-$C_4$ substituted with halogen, and both X and X' are oxygen.

16. A composition according to claim 14 which is 2-chloroacetoxyethyl 5-(2-chloro-4-trifluoromethylphenoxy)-2-nitrobenzoate.

17. A composition according to claim 14 which is 2-(aryloyloxy)ethyl 5-(2-chloro-4-trifluoromethylphenoxy)-2-nitrobenzoate.

18. A composition according to claim 14 which is 2-(trifluoroacetoxy)ethyl 5-(2-chloro-4-trifluoromethylphenoxy)-2-nitrobenzoate.

19. A composition according to claim 14 which is 2-(methoxyacetoxy)-ethyl 5-(2-chloro-4-trifluoromethylphenoxy)-2-nitrobenzoate.

20. A method of controlling undesirable plant growth which comprises applying to the area in which growth is to be controlled a growth controlling amount of the herbicidal composition of claim 14.

21. A method according to claim 20 wherein said control is achieved during growing a soybean, rice or cotton crop.

22. A compound according to claim 1 wherein X is —$NR_5$ and X' is oxygen.

23. A compound according to claim 1 wherein X is —$NR_5$, X' is oxygen, Z is a direct bond, and Y is nitro.

24. A compound according to claim 1 which is N-[2-(acetoxy)ethyl]-N-methyl 5-(2-chloro-4-trifluoromethylphenoxy)-2-nitrobenzamide.

25. A selectively herbicidal composition comprising an effective amount of a compound of the formula of claim 22, and an agronomically acceptable carrier.

26. A selectively herbicidal composition comprising an effective amount of a compound of the formula of claim 23, and an agronomically acceptable carrier.

27. A selectively herbicidal composition comprising an effective amount of a compound of the formula of claim 4, and an agronomically acceptable carrier.

28. A method of selectively controlling undesirable plant growth pre-emergence or post-emergence growth of a corn, rice, soybean, wheat, sorghum or cotton crop which comprises applying to the area in which growth is to be controlled a growth controlling amount of the herbicidal composition of claim 25.

29. A method according to claim 28 wherein said composition is of the formula of claim 27.

30. A method of controlling weed growth in an area of soybean crop growth by applying to said area a weed controlling amount of the herbicide of claim 1.

31. The method of claim 30 which comprises applying to the area of soybean crop, a weed phytotoxic amount of 2-(methoxyacetoxy) ethyl-5-(2-chloro-4-trifluoromethylphenoxy)-2-nitrobenzoate in an agronomically acceptable carrier.

32. The compound of claim 1 wherein $R_2$ is a saturated straight or branched chain aliphatic radical $C_1$-$C_8$ unsubstituted with halogen, trihalomethyl, cyano, nitro, hydroxy, acetoxy, alkoxy, thioalkoxy or aryl; an aryl radical optionally substituted with halogen, trihalomethyl, cyano, nitro, alkyl, alkoxy or hydroxy; a cyclic alkylene or alkylene ring $C_3$-$C_6$ optionally substituted with halogen, trihalomethyl, hydroxy, alkyl, alkoxy or cyano.

* * * * *